(12) United States Patent
Wahl et al.

(10) Patent No.: US 8,129,991 B2
(45) Date of Patent: Mar. 6, 2012

(54) ANATOMICAL FIXTURE FOR MAGNETIC RESONANCE POSITION IMAGING

(75) Inventors: Hugh Wahl, Stonybrook, NY (US); Arto Cinoglu, Oceanside, NY (US); Cristian Balica, Middle Village, NY (US); William H. Wahl, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 681 days.

(21) Appl. No.: 11/227,817

(22) Filed: Sep. 15, 2005

(65) Prior Publication Data
US 2006/0173278 A1 Aug. 3, 2006

Related U.S. Application Data

(60) Provisional application No. 60/630,691, filed on Nov. 24, 2004.

(51) Int. Cl.
*G01V 3/00* (2006.01)
*A61B 5/055* (2006.01)

(52) U.S. Cl. ........ 324/318; 324/307; 324/309; 324/321; 324/322; 600/407; 600/410; 600/415

(58) Field of Classification Search .......... 600/410, 600/415, 417, 421, 422, 429; 128/877, 878, 128/845, 846, 869, 870, 876; 324/307, 309, 324/318, 319, 322, 321; 482/141–144, 148, 482/907, 908, 93–97; 602/17–19, 32, 36; 378/17, 20
See application file for complete search history.

(56) References Cited

U.S. PATENT DOCUMENTS

| | | | |
|---|---|---|---|
| 3,867,634 A * | 2/1975 | Hounsfield | 378/18 |
| 4,296,761 A * | 10/1981 | Tyo | 602/16 |
| 4,534,358 A | 8/1985 | Young | |
| 5,065,761 A | 11/1991 | Pell | |
| 5,081,665 A | 1/1992 | Kostich | |
| 5,171,296 A | 12/1992 | Herman | |
| 5,221,902 A | 6/1993 | Jones et al. | |
| 5,274,332 A | 12/1993 | Jaskolski et al. | |
| 5,379,768 A * | 1/1995 | Smalen | 600/410 |
| 5,520,181 A | 5/1996 | Kreidler et al. | |
| 5,566,681 A | 10/1996 | Manwaring et al. | |
| 5,680,861 A | 10/1997 | Rohling | |
| 5,735,278 A | 4/1998 | Hoult et al. | |
| 5,836,878 A | 11/1998 | Mock et al. | |
| 5,855,582 A | 1/1999 | Gildenberg | |
| 5,899,859 A * | 5/1999 | Votruba et al. | 600/415 |
| 5,947,981 A | 9/1999 | Cosman | |
| 5,986,531 A | 11/1999 | Carrozzi et al. | |
| 5,988,173 A | 11/1999 | Scruggs | |
| 6,138,302 A | 10/2000 | Sashin et al. | |

(Continued)

FOREIGN PATENT DOCUMENTS
JP  1-305937  12/1989
(Continued)

OTHER PUBLICATIONS

Supplementary European Search Report, EP 05798872, dated Jul. 17, 2009.

*Primary Examiner* — Tse Chen
*Assistant Examiner* — Vani Gupta
(74) *Attorney, Agent, or Firm* — Lerner, David, Littenberg, Krumholz & Mentlik, LLP

(57) ABSTRACT

Fixtures for immobilizing a patient during magnetic resonance imaging.

21 Claims, 20 Drawing Sheets

U.S. PATENT DOCUMENTS

| | | |
|---|---|---|
| 6,414,490 B1 | 7/2002 | Damadian et al. |
| 6,684,096 B2 | 1/2004 | Schmit et al. |
| 6,750,653 B1 * | 6/2004 | Zou et al. .................. 324/318 |
| 6,882,377 B2 | 4/2005 | Kohtaka et al. |
| 7,030,612 B1 * | 4/2006 | Damadian et al. ............ 324/318 |
| 7,061,242 B2 * | 6/2006 | Ochi et al. .................. 324/318 |
| 7,196,519 B2 * | 3/2007 | Damadian ................... 324/318 |
| 2002/0032927 A1 | 3/2002 | Dinkler |
| 2003/0204136 A1 | 10/2003 | Green et al. |
| 2004/0030241 A1 | 2/2004 | Green et al. |
| 2004/0220467 A1 * | 11/2004 | Bonutti ........................ 600/407 |

FOREIGN PATENT DOCUMENTS

| | | |
|---|---|---|
| WO | WO-97/07896 | 3/1997 |

* cited by examiner

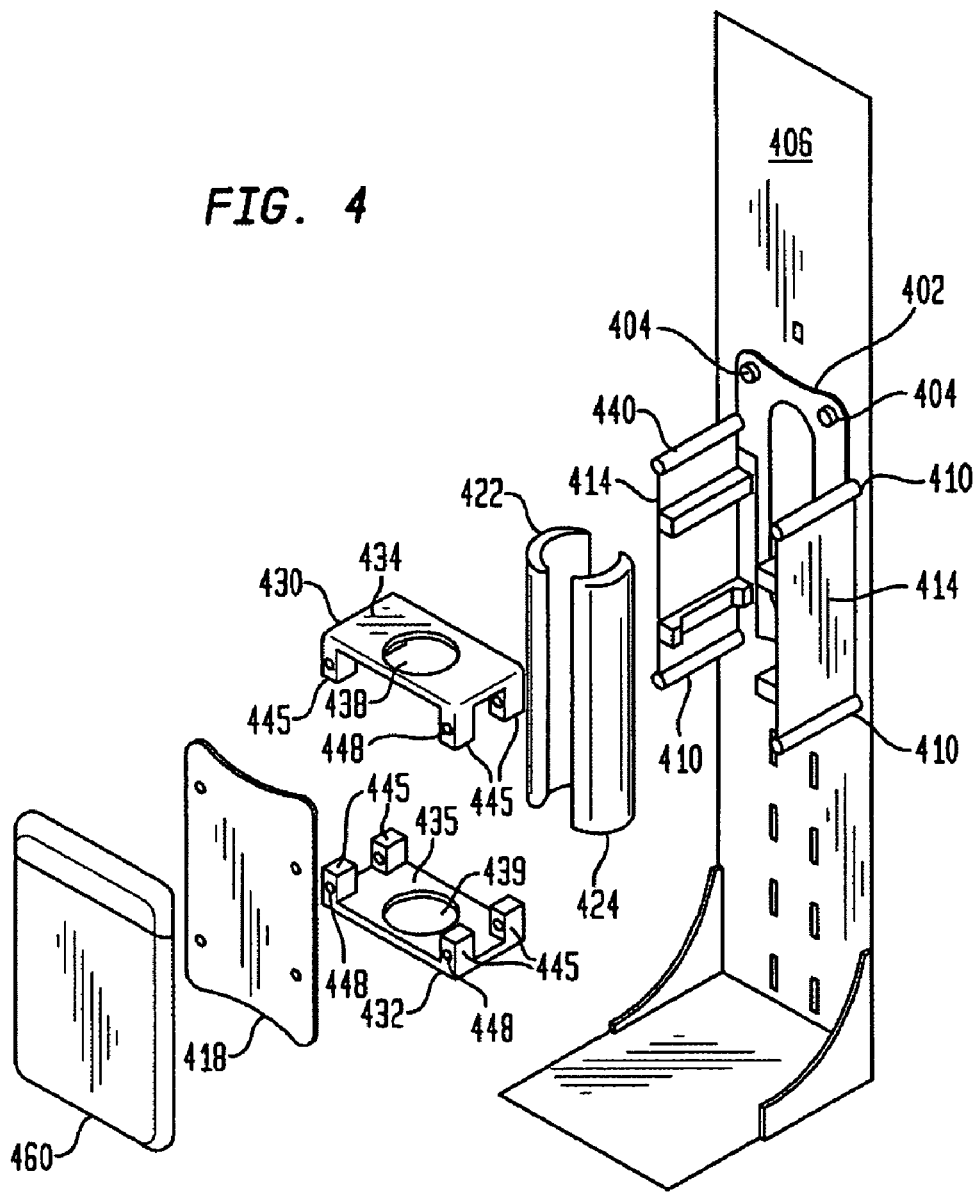

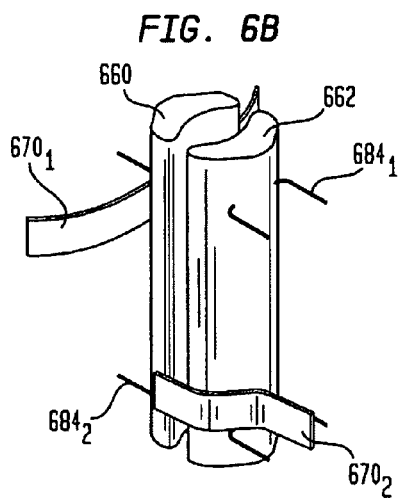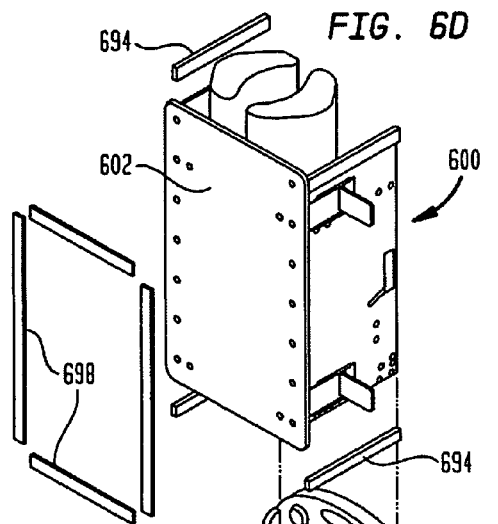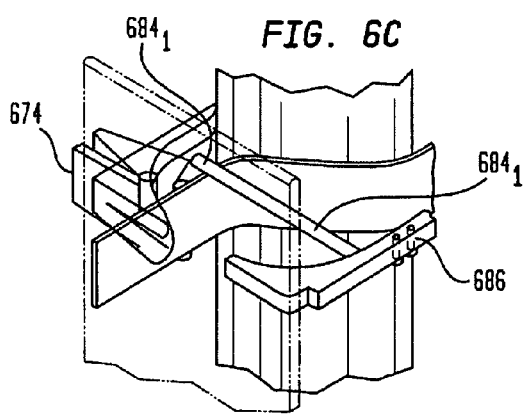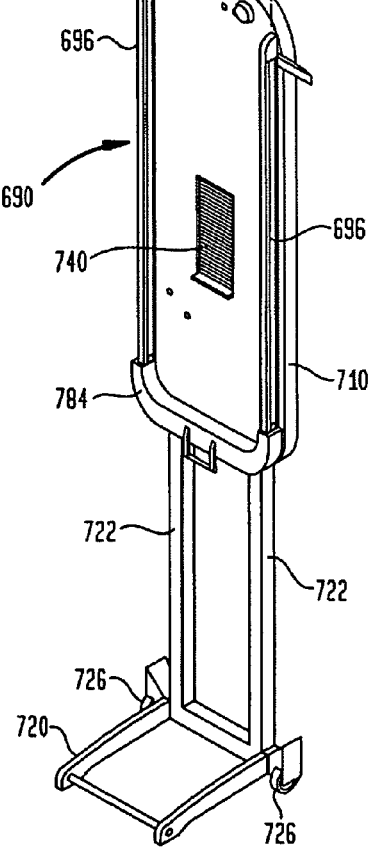

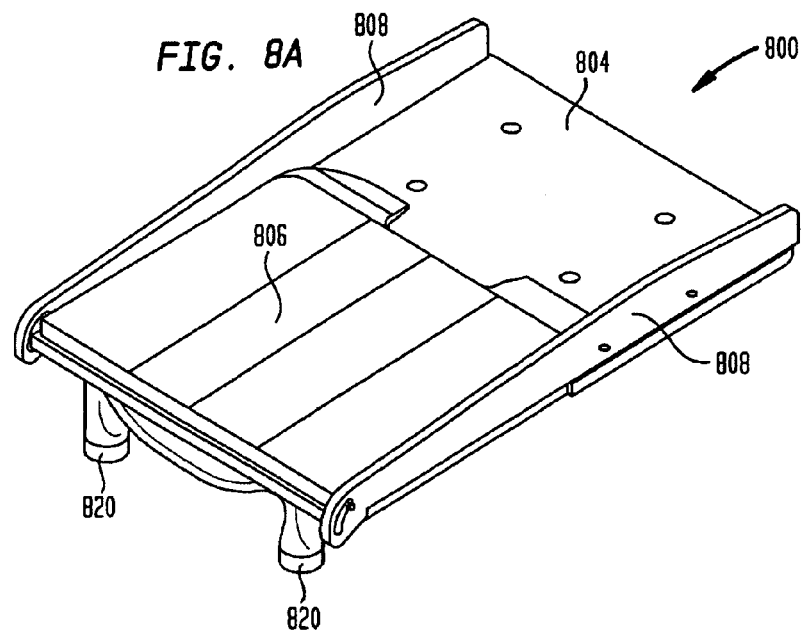
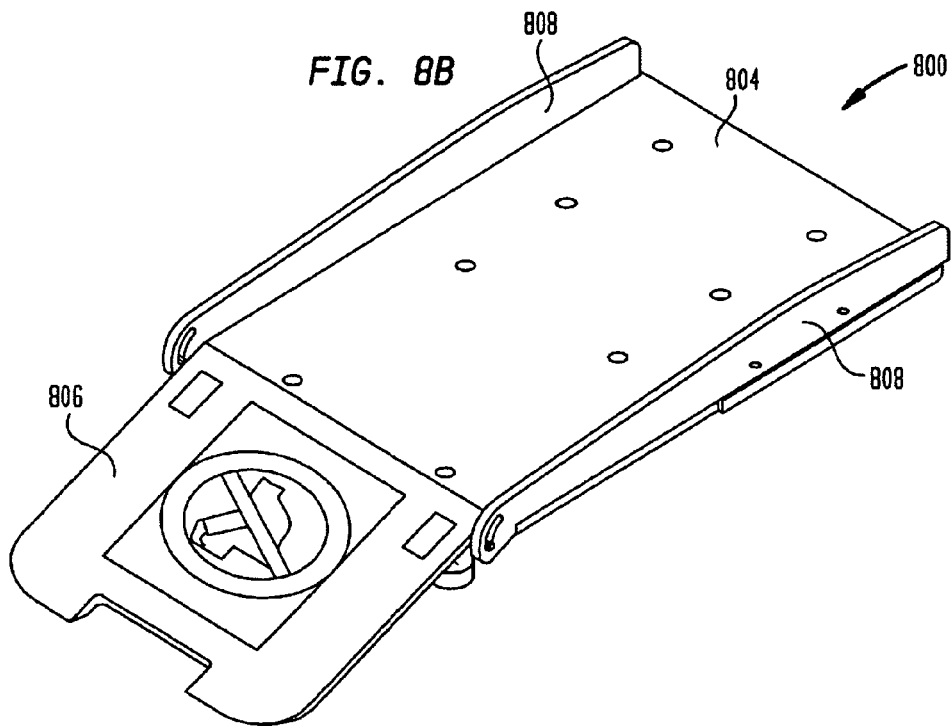

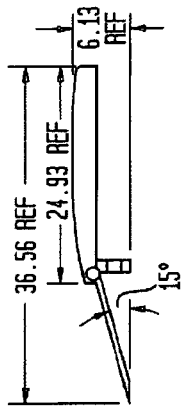
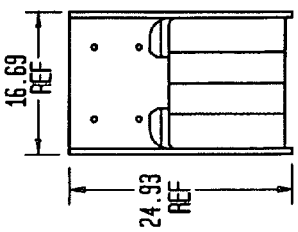
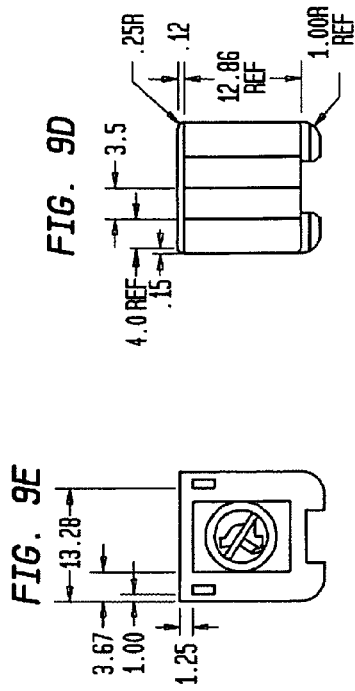
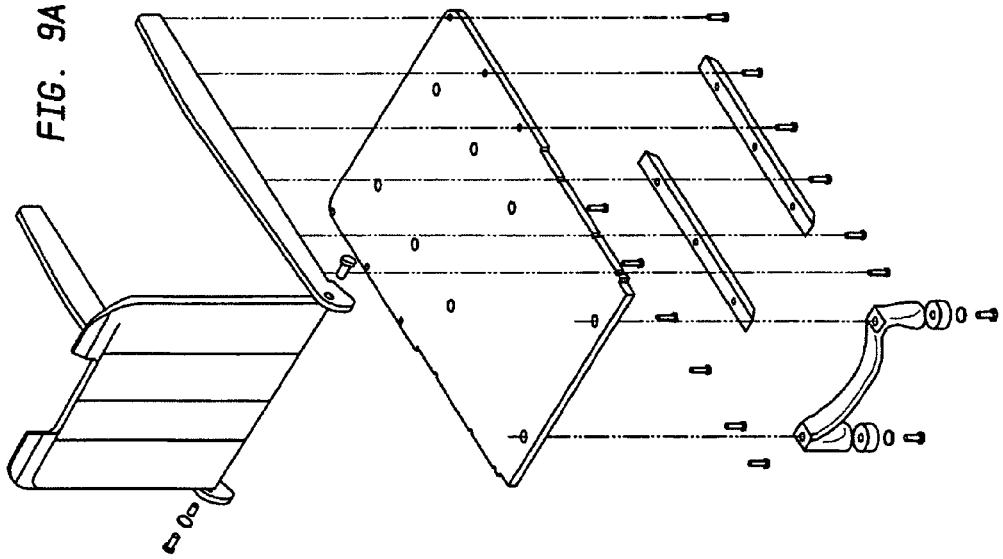

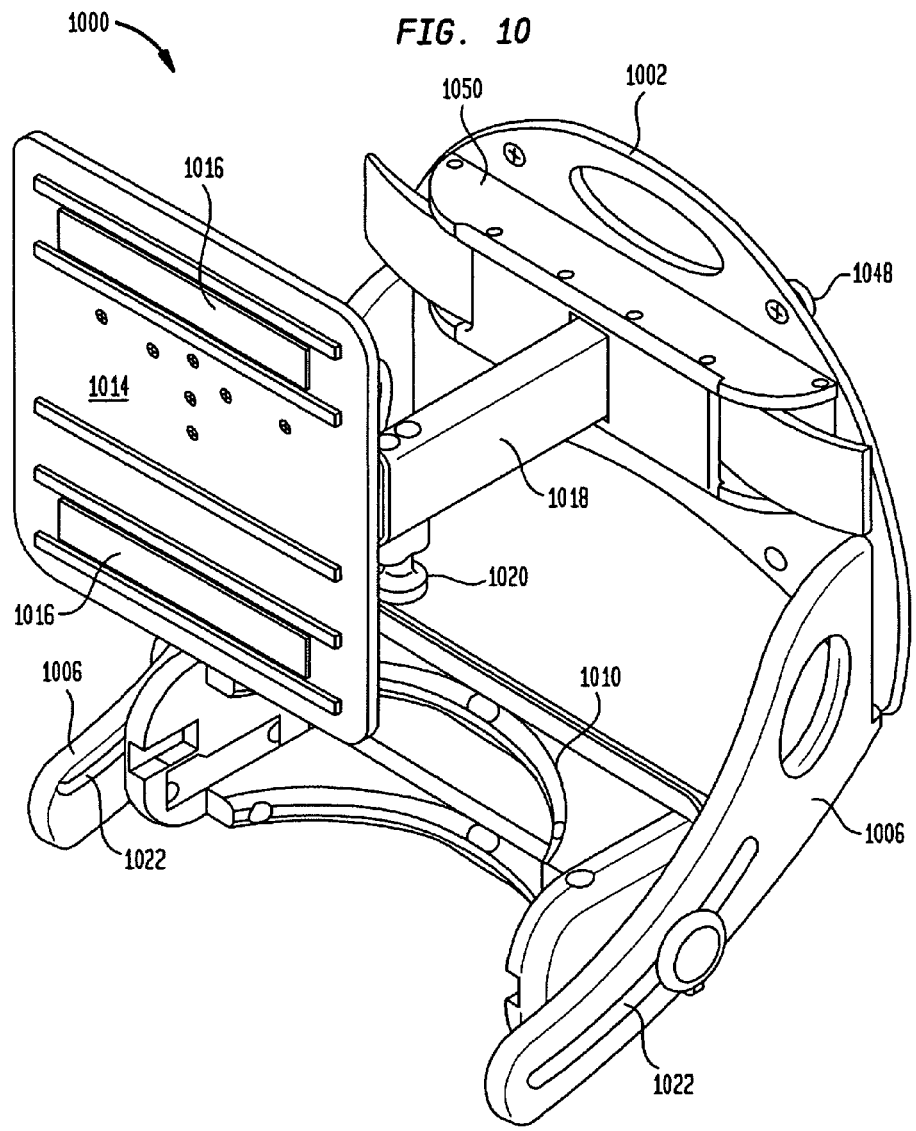

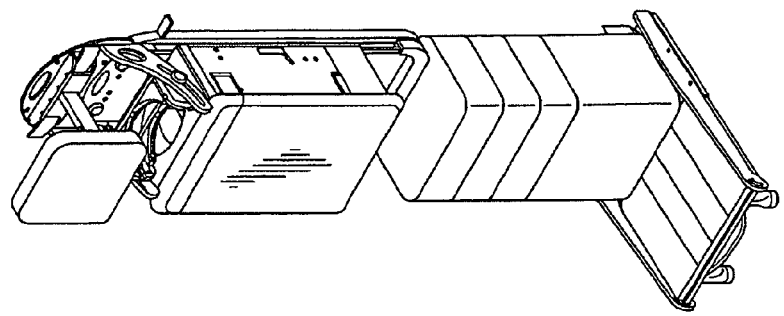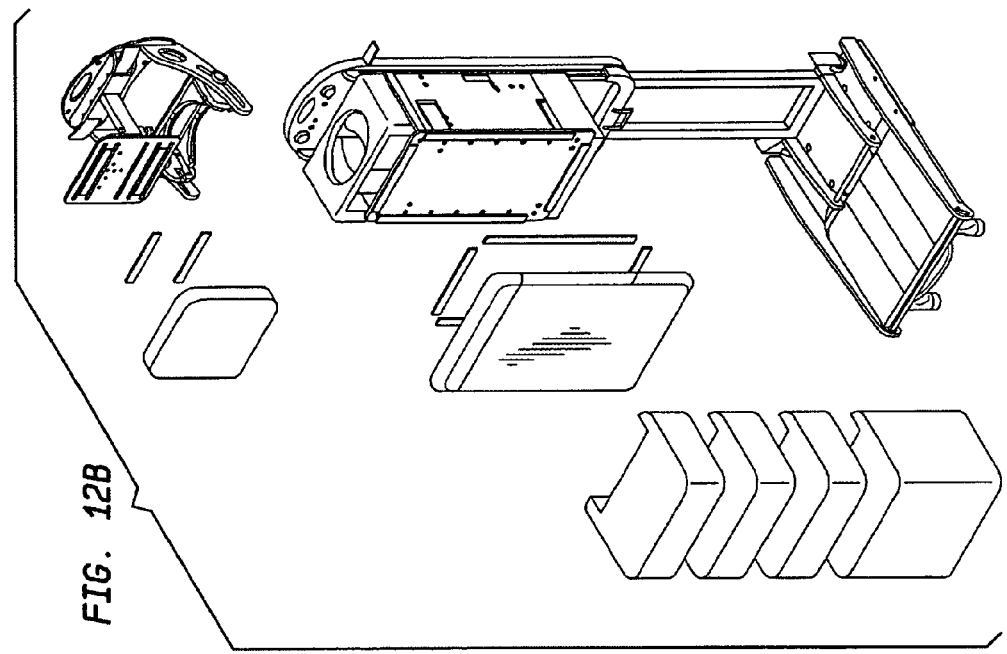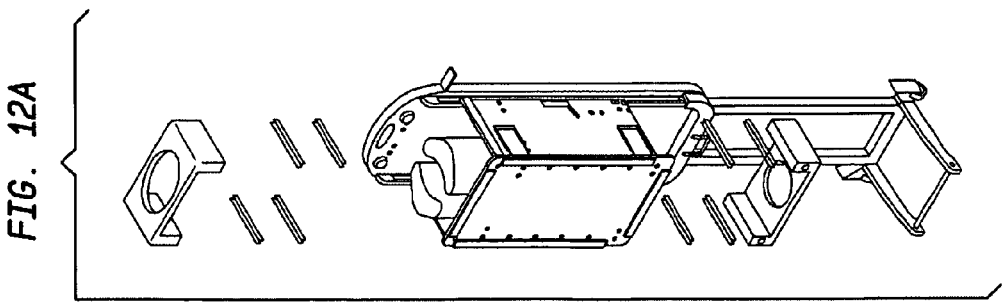

ANATOMICAL FIXTURE FOR MAGNETIC RESONANCE POSITION IMAGING

CROSS-REFERENCE TO RELATED APPLICATIONS

The present application claims the benefit of the filing date of U.S. Provisional Application No. 60/630,691, filed Nov. 24, 2004, the disclosure of which is hereby incorporated herein by reference.

BACKGROUND OF THE INVENTION

The present application relates to magnetic resonance imaging systems, apparatus and procedures and, in particular, to apparatus and procedures for immobilizing a portion of a patient's anatomy during imaging.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are a dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to image the patient on a bed that remains horizontal throughout the procedure.

Advancement in magnetic resonance imaging has resulted in imaging apparatus that supports a patient in any position between a vertical position and a horizontal position. As described in greater detail in commonly assigned U.S. Pat. Nos. 6,414,490 and 6,677,753, the disclosures of which are hereby incorporated by reference herein, a magnetic resonance imaging system can be provided with a patient support, such as a bed or table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

The position of a patient during magnetic resonance imaging may affect or limit the imaging information obtained. A patient may exhibit a symptom if oriented in an upright or weight bearing position and no symptom if oriented in a recumbent or horizontal position. For example, it may be necessary to image a patient in an upright or gravity bearing position to discern a symptom and provide a diagnosis for injuries relating to, for example, the neck, spine, hip, knee, foot or ankle areas of the anatomy.

In addition to a patient's position, movement by a patient during imaging may also affect the images obtained. In fact, magnetic resonance imaging procedures generally require the patient to remain perfectly still during imaging. Movement by a patient typically results in motion artifacts appearing in the image. This often results in rescanning, which reduces the throughput of the imaging system.

There are many factors that contribute to movement on the part of a patient. For example, a patient positioned in a weight-bearing upright posture may find it more difficult to remain still during imaging. In addition, the anxiety level of a patient may affect how still a patient remains during imaging. In general, those magnets that place the patient in the bore of the magnet during imaging tend to add to the patient's anxiety level because of the closed-in and tight environs. A more relaxed patient tends to move less during imaging. Even when relaxed, the patient may not be able to keep still depending on their age, the portion of anatomy of interest (e.g., the spine or shoulder) or the degree of pain that they may be experiencing.

Of utility then are methods ands systems that address these needs and provide ways of better immobilizing a patient during an MRI scan.

SUMMARY OF THE INVENTION

In one aspect, the present invention is a method for performing magnetic resonance imaging. The method preferably comprises attaching a fixture to a patient support apparatus associated with a magnetic resonance imaging magnet, the magnet defining a static magnetic field direction, and positioning a patient adjacent the patient support apparatus such that an arm of the patient is inserted in the fixture and the patient's anterior to posterior axis is parallel to the static field direction. The method further preferably comprises scanning a portion of the patient's anatomy.

Further in accordance with this aspect of the present invention, the method further comprises rotating the patient support to a non-upright position.

The method may further desirably comprise supporting the patient's head and feet against the patient support apparatus and rotating the patient to a recumbent position.

Further in accordance with this aspect of the present invention, supporting the patient's head preferably comprises inserting a second fixture to the patient support adjacent the patient's head.

In another aspect, the present invention is a fixture. The fixture preferably comprises a base plate, a pair of sidewalls, a top member and a bottom member assembled to form an enclosure having at least one opening accessible by an arm of a patient. The fixture is preferably capable of being mounted to a bed associated with a magnetic resonance scanner such that during magnetic resonance imaging movement of the patient's anatomy is reduced. The fixture may also include a pair of semi-circular cylindrical members disposed within the enclosure that operate as a sleeve for receiving the patient's arm.

In accordance with this aspect of the present invention, the fixture further comprises a station that is operable to mount the fixture to the bed. In addition, the station preferably includes a pulley assembly that moves the sidewalls, top and bottom members relative to the bed in a direction substantially parallel to a lengthwise direction defined by the bed.

Further in accordance with this aspect of the present invention, the fixture may further include an arm disposed between the sidewalls at a predetermined distance away from the base plate. The arm is preferble operable to engage one of a plurality of ridges on the station such that fixture may be moved relative to the bed in a direction substantially parallel to a lengthwise direction defined by the bed at predetermined steps defined by the distance between the ridges.

Further in accordance with this aspect of the present invention, the sidewalls, top and bottom members are desirably movable relative to the base plate in a direction substantially parallel to a lengthwise direction defined by the bed. In addition, at least one of the sidewalls is mounted to a bracket, the bracket being connected to the base plate through one or more biasing members that urge the sidewalls, top and bottom members toward the base plate.

Furthermore, the fixture may desirably further comprise at least one mounting rack having a first portion fixably mounted to the base plate and second portion detachably mounted to the first portion and the bracket such that the sidewalls, top and bottom members are movable relative to the base plate in a direction substantially parallel to a lengthwise direction defined by the bed.

In accordance with this aspect of the present invention, the fixture may further comprise one or more mounting knobs attached to the base plate, the mounting knobs being insertable in one or more slots provided on the bed.

In another aspect, the present invention is a fixture for magnetic resonance imaging. The fixture desirably comprises a base plate, a pair of sidewalls, a top member and a bottom member assembled so to form an enclosure having at least one opening accessible by an arm of a patient; and a sleeve for receiving the patient's arm. It is further preferable that the fixture be mountable to a bed of a magnetic resonance scanner such that during magnetic resonance imaging movement of the patient's is reduced.

Further in accordance with this aspect of the present invention, the sidewalls, top and bottom members are preferably movable relative to the base plate in a direction substantially parallel to a lengthwise direction defined by the bed.

Further still, it is preferably that at least one of the sidewalls is mounted to a bracket, the bracket being connected to the base plate through one or more biasing members that urge the sidewalls, top and bottom members toward the base plate. In addition, the fixture may further comprise at least one mounting rack having a first portion fixably mounted to the base plate and second portion detachably mounted to the first portion and the bracket such that the sidewalls, top and bottom members are movable relative to the base plate in a direction substantially parallel to a lengthwise direction defined by the bed.

In another aspect, the present invention comprises yet another fixture. The fixture preferably comprises a base plate and a pair of sidewalls assembled so as to form an enclosure having at least one opening; and a pair of semi-circular cylindrical members disposed within the enclosure through the at least one opening so as to operate as a sleeve for receiving a patient's arm, and wherein the fixture is capable of being mounted to a bed of a magnetic resonance scanner such that during magnetic resonance imaging the fixture reduces movement of the patient's anatomy.

In yet another aspect, the present invention is a magnetic resonance imaging system. The system comprises a magnet capable of generating a static magnetic field that defines an imaging volume; a patient support apparatus capable of supporting a patient and positionable in a receiving space defined by the magnet such that a portion of the patient's anatomy can be placed in the imaging volume; and a first fixture having a base plate and a pair of sidewalls assembled so as to form an enclosure having at least one opening, the at least one opening being operable to receive a patient's arm.

BRIEF DESCRIPTION OF THE DRAWINGS

FIG. 4 illustrative depicts an exploded view of a system in accordance with an aspect of the present invention.

FIG. 6B illustratively depicts a portion of the apparatus of FIG. 6A in accordance with an aspect of the present invention.

FIG. 6C illustratively depicts exploded views of a portion of the apparatus of FIG. 6A in accordance with an aspect of the present invention.

FIG. 6D is an assembly diagram that illustratively depicts a system that includes the apparatus of FIG. 6A and an additional apparatus in accordance with an aspect of the present invention.

FIGS. 8A and 8B illustratively depict an apparatus in accordance with an aspect of the present invention.

FIGS. 9A through 9E illustratively depict various assembly views of the apparatus of FIG. 8 in accordance with an aspect of the present invention.

FIG. 10 illustratively depicts an apparatus in accordance with an aspect of the present invention.

FIG. 12 illustratively depicts various assembly views of a system in accordance with an aspect of the present invention.

DETAILED DESCRIPTION

Figure 1:
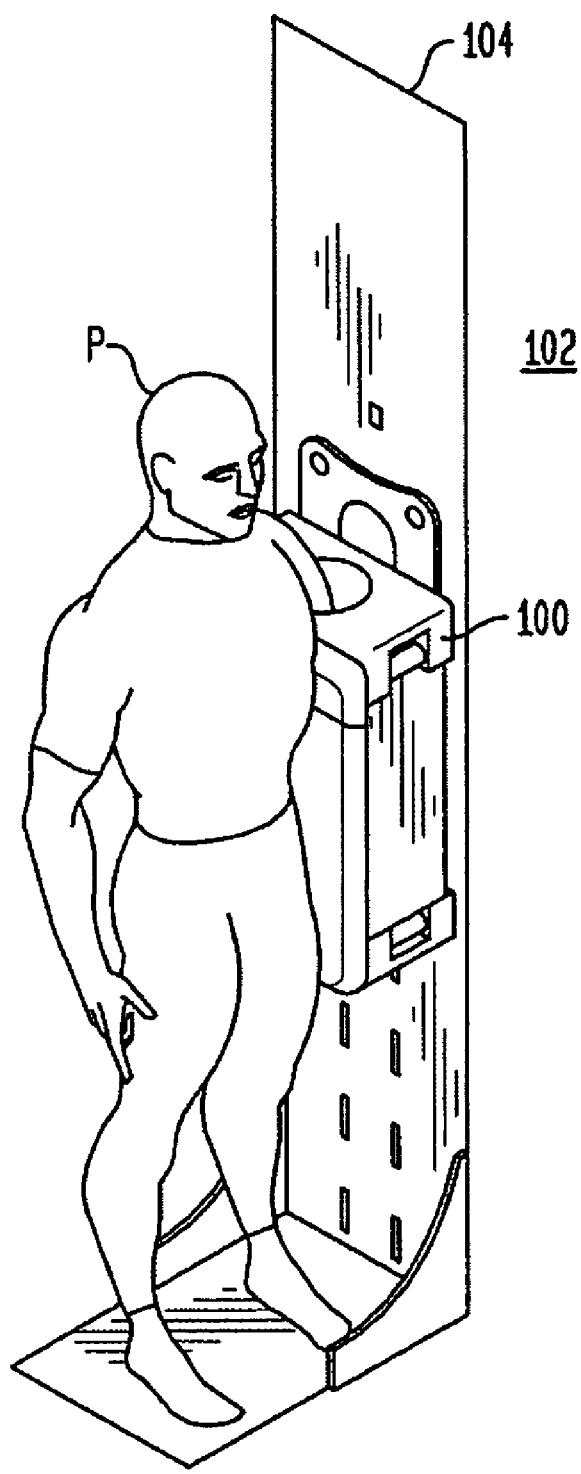
FIG. 1 illustratively depicts a system in accordance with an aspect of the present invention.

FIG. 1 illustratively depicts a fixture 100 that forms part of a system 102 in accordance with an aspect of the present invention. As shown, in the system 102, the fixture 100 is preferably affixed to a bed or patient support 104 so as to allow a patient P to insert an arm into the fixture 100 thereby allowing for immobilization of an arm of the patient P during imaging. As discussed, patient motion degrades the quality of images obtainable in magnetic resonance imaging sometimes to levels where the images are unreadable. The fixture 100 immobilizes the patient's arm and also assists in aligning the anatomical area of interest in the magnet's isocenter. As is discussed in further detail below, the fixture 100 may also be used to immobilize other portions of a patient's anatomy, e.g., foot, ankle or elbow, that are being imaged. Fixtures of this type also allow the patient to be tilted away from a fully upright vertical position during the imaging process while still allowing for a reduction in patient movement. This advantageously allows the patient to be imaged in a variety of different orientations, in addition to the standing position.

Figure 2:
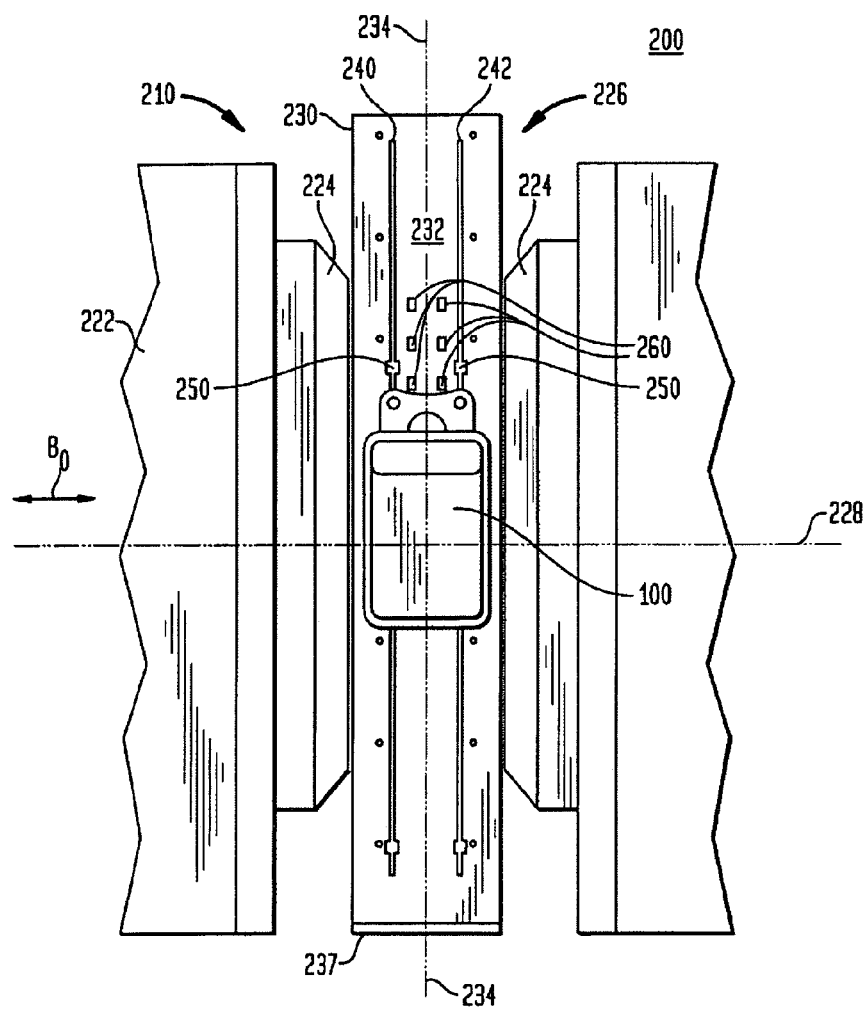
FIG. 2 illustratively depicts a system in accordance with an aspect of the present invention.

The fixture is preferably used in conjunction with the support device 104 and a magnet that can generate a substantially horizontal magnetic field and allows a patient to be imaged in an upright position. Such a magnet may comprise a magnet, for example, as shown in FIG. 2 and as described, for example, in commonly assigned U.S. Pat. Nos. 6,414,490 and 6,677,753, the disclosures of which are incorporated by reference herein.

In particular, FIG. 2 depicts a front view of magnetic resonance imaging system 200 and fixture 100 in accordance with an embodiment of the present invention. The system 200 includes a magnet resonance imaging apparatus 210, which includes a magnet 222 comprising a pair of opposed elements 224 defining a patient-receiving space 226 between them. In the particular magnet illustrated, the opposed elements are pole faces. Other types of magnets may also be used and may comprise superconducting or resistive electromagnet coils or other structures. The magnet 222 is arranged to provide a magnetic field surrounding a magnet axis 228 within patient-receiving space 226. The magnet axis 228, as well as the magnetic field axis Bo, extends in a substantially horizontal direction as shown.

The magnetic resonance imaging apparatus 210 further includes a patient support 230 having a patient support surface 232. The patient support 230 is generally elongated in a longitudinal direction 234. As shown, the patient support surface 232 may be oriented to lie in a generally vertical plane, which results in the longitudinal direction extending generally vertically. It is also possible, however, to rotate the patient support 230 so that the longitudinal direction extends in a substantially horizontal direction, or any direction between horizontal and vertical. The widthwise or lateral dimension of the patient-receiving surface is transverse to the longitudinal direction 234 and extends parallel to the magnet axis 228. The lateral dimension is slightly less than the dimension of the patient-receiving space 226 between the elements 224. A footrest 237 desirably projects from one end of the patient-receiving surface 232 and is generally used as a standing surface.

Figure 3:
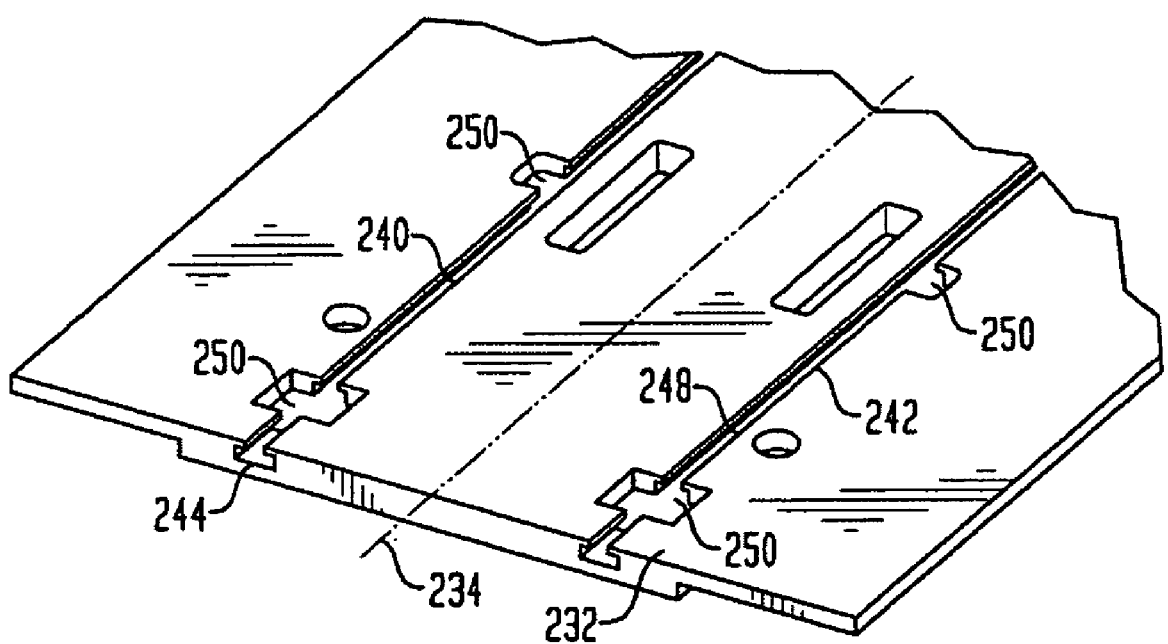
FIG. 3 illustratively depicts a portion of patient receiving apparatus in accordance with an aspect of the present invention.

As also shown in FIG. 2, the system includes the fixture 100. The fixture 100 is preferably mounted to the patient support via a pair of slots 240, 242. As shown in greater detail in FIG. 3, the slots 240 and 242 are generally T-shaped 244 in cross section. Thus, each slot has a narrow top portion 248 where the slots open to the surface 232 remote from the opening of the slot. Pockets 250 are provided in pairs along the lengths of the slots 240 and 242. These pockets are generally wider than the narrow top portion 248. The surface 232 further includes a pair of generally rectangular pockets 250 disposed opposite each other along the lateral direction of the surface 232. In addition to the foregoing, commonly assigned U.S. patent application Ser. No. 10/131,843, the disclosure of which is hereby incorporated by reference, discloses additional methods for connecting structures to the support surface. The fixture 100 is preferably slidably mounted to the patient support 230 via the slots 240, 242, thereby allowing the fixture 100 to be suitably adjusted to the height of the anatomical area of interest being imaged, e.g., the shoulder, elbow or knee.

As shown in FIG. 4, a fixture 400, in accordance with an aspect of the present invention, includes a back plate 402 that is affixable to a patient support 406. The back plate 402 is preferably affixed to the patient support 406 using a pair of locking knobs 404. In addition to serving as the mounting member, the back plate 402 serves as a support base for the other structural elements that comprise the fixture 400 including support legs 410, and side plates 414. As shown, each of the support legs 410 are mounted between the back plate 402 and a front plate 418 to form a substantially rectangular frame with each of the plates 402, 418 serving as back and front walls, respectively. Each side plate 414 is mounted between a respective pair of support legs 410. As such, the side plates 414 serve as sidewalls in the rectangular frame. When the back plate 402, side plates 414 and front plate 418 are in an assembled condition, a box like structure is formed (see FIG. 1).

A pair of left and right semi-cylindrical members 422, 424 is housed within the box like structure and serves as immobilization and guide members for that portion of the patient's anatomy that is inserted into the fixture 400. In the particular fixture or apparatus 400, a patient's arm is preferably inserted into the fixture 400. Specifically, in the assembled condition, the members 422, 424 are housed next to each other so as to form a cylindrical opening for receiving a portion of the patient's anatomy. In that regard, the members 422, 424 are preferably made from foam or other magnetically translucent material, such as rubber or plastic that provides firm, but comfortable support for the patient. In addition to being magnetically translucent, the material must also not be capable of producing a NMR field or signal.

The fixture further preferably comprises a pair of end members 430, 432. One end member 430 forms the top of the fixture 400 in the assembled condition. The other end member 432 forms the bottom of the fixture 400 in the assembled condition. Each end member 430, 432 preferably includes a planar surface portion 434, 435 that includes an opening 438, 439, respectively. The openings allow access to the interior of the fixture 400. Each end member 430, 432 also includes legs 445. Each leg 445 includes an opening 448 for receiving a support leg 410. The end members 430, 432 may be made such that they are interchangeable and usable at either end of the fixture 400. The fixture may also include a front panel 460 that can be detachable affixed to the front plate 418. The end members 430, 432 may be made from foam, rubber, vinyl or plastic. The front panel 460 is preferably made of foam, but may be made from soft rubber, plastic, or a cushiony material. As discussed above, the materials used to make the various portions of the fixture should be magnetically translucent and not be capable of producing an NMR field or signal.

In the assembled position, the fixture 400 allows a human subject to insert an arm into the fixture 400, such as shown in FIG. 1. The fixture 400 (or 100) then assists in immobilizing the patient's arm and anatomy during scanning. This results in reducing motion artifacts during scanning. Patient motion degrades imaging quality, sometimes to a level where the images cannot be read. As such, the fixtures 100, 400 improve the imaging process by increasing the yield rate with respect to image quality, thereby improving throughput.

With reference to FIGS. 1 through 4, a method of using the apparatus or fixture 400 will now be described. Prior to a patient inserting an arm into the fixture 400, the fixture is placed at an approximate height that will allow the patient to stand on the footrest 237 while comfortably inserting an arm into the fixture 400. The patient may then enter the patient receiving space and insert an arm into the fixture. If the fixture is not at an appropriate height for the patient, an operator may re-adjust the height of the fixture accordingly. With the patient arm in the fixture, imaging may then proceed with the patient in a standing position. Imaging may also proceed with the patient support 104 (230 or 406) rotated such that the patient is no longer in the standing position. For imaging to take place with the patient support rotated, the feet of the patient will need to be supported so that the patient can lie on their side. As is discussed in greater detail below, this may be accomplished by placing one or more support structures between the patient's legs and the surface of the patient support. The support structures may comprise foam mats or cushions.

Figure 5A:
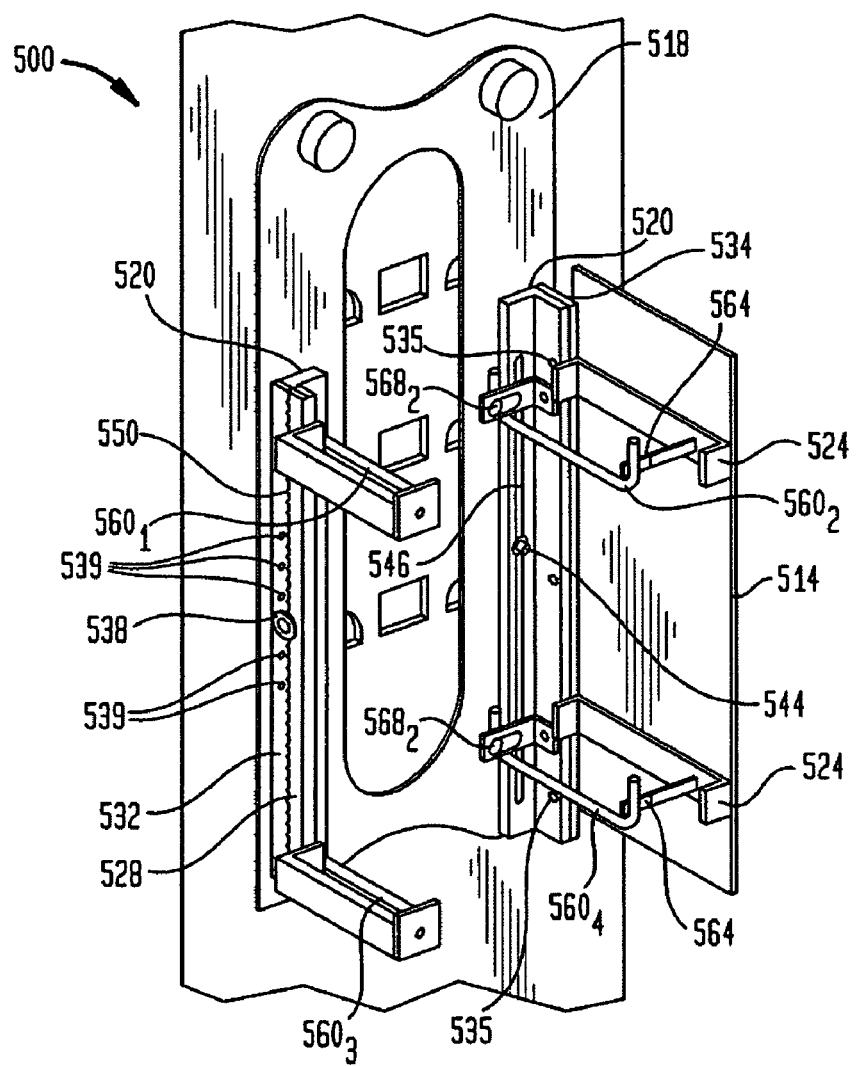
FIG. 5A illustratively depicts the internal structure of an apparatus in accordance with an aspect of the present invention.

Turning now to FIG. 5A, there is shown an exploded view of a fixture 500 that reveals additional details of its structure. In particular, a side plate 514 is mounted to a base plate 518 via a mounting rack 520. The side plate 514 is connected to the mounting rack 520 through U-shape brackets 524. The side plate is preferably connected to the mounting rack 520 using a nut and bolt assembly, but any fastener may do. As the fixture 500 is to be used in a magnetic resonance imaging apparatus, any fasteners or other materials that are used may be made from brass, plastic or any other suitable material as discussed above.

Figure 5B:
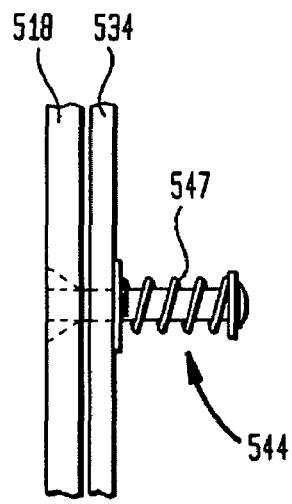
FIG. 5B depicts an exploded view of a portion of the apparatus of FIG. 5A.

The mounting rack 520 includes a front rack 528, a back rack 532 and an L-shaped bracket 534. The L-shaped bracket 534 is preferably affixed to the front rack using two or more screws 535. The back rack 532 is fixed relative to the back plate 518 and attached thereto using a plurality of fasteners or screws. A locking mechanism 538 is also connected to the mounting rack 520 and preferably inserted through back rack 532. The fixture further includes a spring mechanism 544. The spring mechanism comprises a nut and bolt assembly that is mounted to the base plate 518 through a slot 546 in the L-shaped bracket 534 using a biasing element 547 (see FIG. 5B). The spring mechanism 544 provides a force that urges the mounting rack 520 against the base plate 518.

Figure 5C:
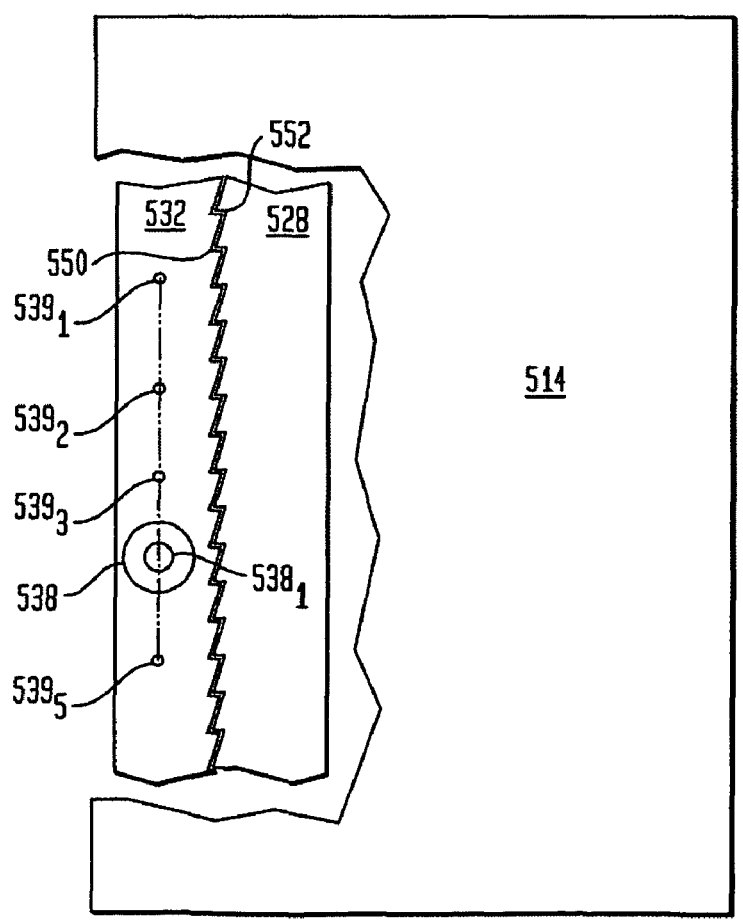
FIG. 5C depicts an exploded view of a portion of the apparatus of FIG. 5A.

As best seen in FIG. 5C, the front and back racks, 528 and 532, each include a side 550, 552 having a plurality of notches or interdental spaces that desirably interlock with each other. Each notched side 550, 552 forms a mating member that when joined together assist in keeping the box-like structure of the fixture in place relative to the base plate. The locking mechanism 538 is centered relative to the width of back rack 532 and aligned with a plurality of holes or notches 539 on back rack 532. The locking mechanism 538 comprises a knob 538, that is connected to pin (not shown). The pin is inserted through the side wall and engages one of the holes 539 when the assembly is locked in place. The knob $538_1$ is accessible on the outer surface of side wall 514.

Returning to FIG. 5A, the fixture 500 also includes a bungee mechanism 558. The bungee mechanism 558 comprises bungee cords $560_1$ through $560_4$. Each bungee cord is secured to U-shaped bracket 524 and the mounting rack 520. As shown, the bungee cords are secured at their distal ends to fingers 564 that protrude from the distal end of the U-shaped bracket 524. The fingers 564 may also protrude from other locations along the U-shaped bracket 524 such as the center, as long as sufficient tension can be maintained on the bungee cords 560. The proximal ends of the bungee cords are secured to the L-shaped bracket 534 by L-shaped mounting members 568. The bungee cords assist in holding sleeves that are inserted in the enclosure.

The spring mechanism 544 and locking mechanism 538 work in conjunction with the front and back racks 528, 532 to allow for height adjustments of the fixture in the lengthwise or longitudinal direction 234 relative to the base plate 518 and the patient support. In particular, when the locking mechanism 538 and inter-mating notches on sides 550, 552 are engaged, the fixture 500 is locked in place relative to the base plate. As best seen in FIG. 5C, the locking mechanism 538 may be unlocked by rotating or pulling knob $^{538}$, such that the pin that forms a part of the locking mechanism 538 is pulled out of one of the holes 539. The holes 539 are formed in back rack 532 and spaced at a predetermined interval depending on the levels of height adjustment desired.

With the pin pulled out the holes 539, the front portion of the fixture 500 (i.e., the side plates, front rack and front plate) may then be pulled away from the base plate 518 and back rack 532 such that the inter-mating teeth on notched sides 550, 552 are disengaged or spaced apart. As the front portion is pulled away from the base plate, the spring mechanism 544 urges L-shaped bracket 534 toward the base plate 518. With the appropriate force applied, the front portion may then be raised or lowered, in general slid, relative to the base plate 518 and back rack 532. In particular, the notched side 552 slides relative to notched side 550 in the longitudinal direction and the L-shaped bracket 534 slides relative to locking mechanism 544 in slot 546. Such adjustment allows the operator to adjust the height of the fixture 500 so that it snugly fits under the arm pit of the patient P so as to provide suitable immobility during imaging.

Put another way, the distance from the underarm of a person, to the floor, varies from patient to patient. This means that the fixture needs to be adjusted for each patient. The steps or notches on racks 528, 532 form male and female steps. Preferably, the rack with the male step is mounted to the front plate (movable bed section), and the rack with the female step is mounted to the back plate (stationary back, which mounts to the system bed or slab). Each rack, male and female, includes the required number of steps to cover an assumed distance (coverage) up and down. The use of springs allowed the racks to be attracted to each other, and engage the male into the female step. To raise, or lower the front section, a user pulls the front plate slightly away from the rear plate, disengaging the racks, raise or lower the front section, then release the front plate and allow the springs to re-engage the racks.

Figure 6A:
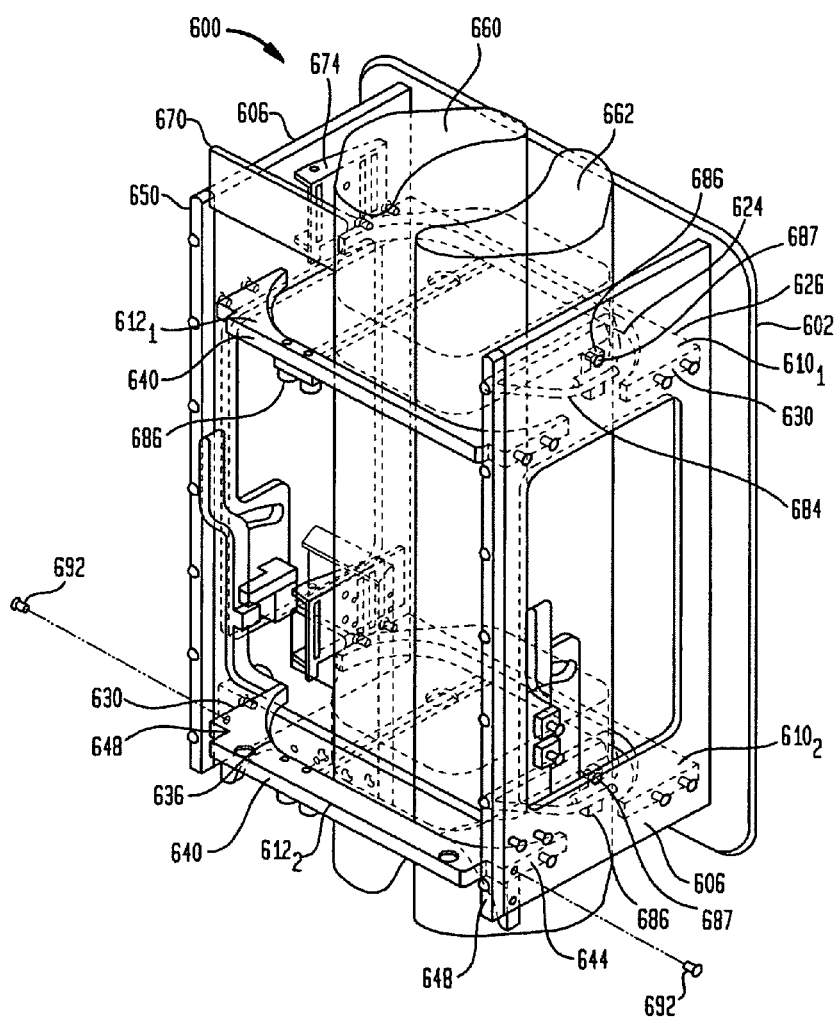
FIG. 6A illustratively depicts an apparatus in accordance with an aspect of the present invention.

Turning now to FIG. 6A, there is shown a fixture 600 in accordance with an additional aspect of the present invention. The fixture 600 includes a base plate 602 and a pair of side plates 606. The fixture 600 further comprises a pair of planar members 610, 612 that together from a top ($610_1$ and $612_1$) and bottom ($610_2$ and $612_2$). Each of the planar members 610 includes an arcuate inner section 624 and a straight side 626 that terminate on sides 630 so as to form a gusset. The planar member 612 also includes an arcuate inner side 636 and a straight side 640 that terminate on sides 644 so as to form a gusset. In the assembled condition, the straight sides 626, 640 are preferably mounted along the outer edge of the box so that the arcuate inner sections 624, 636 together form a substantially oval opening, as shown. The sides 630 are preferably mounted to the side walls 606 using fasteners, such as screws, in the assembled condition. Each corner 648 of the planar member 612 includes an L-shaped notch that mates with a guide rail as discussed below.

The fixture 600 further includes a pair of semi-circular members 660, 662 that together form a cylindrical opening into which an arm of a patient may be inserted. The members 660, 662 function to hold the patient's arm in place and are preferably constructed from a firm but comfortable material. The material may comprise foam, rubber or plastic. In addition to being magnetically translucent, the material should not interfere with the imaging process, i.e., should not generate an NMR field or signal. The fixture 600 also includes a strap 670 and buckle assembly 674, which assists in securing the pair of semi-circular members 660, 662 to the patient's arm.

Additional details of the fixture 600 are shown in FIG. 6B through 6D. In particular, FIG. 6B is an exploded view of the semi-circular members 660, 662. The members 660, 662 are preferably constructed from foam and molded so as to fit snugly into the opening of the fixture 600. A pair of straps $670_1$, $670_2$ is attached to the members 660, 662 at their upper and lower ends. The straps $670_1$, $670_2$ are also attached to the fixture 600 using bungee cords $684_1$. The strap and bungee cord are assembled as follows. The straps and bungee cords are cut to their respective desired lengths. The ends of the straps and cords may be melted with a soldering iron to prevent fraying. Holes are burned through the straps and a bungee cord is slid through the holes. The bungee cord is then inserted through holes in the member 660, holes in member 662 and through additional holes in the strap. As best seen in FIGS. 6A and 6C, the bungee cord is inserted through the inside of members 660, 662 exiting for a predetermined distance around the strap and attached at its ends to clamps 686 and screws 687. The ends of the straps are preferably slid through the side walls 606 of the fixture and made accessible to an operator. One end of the strap may be connected to buckle assembly 674 such that it may used to secure the members 660, 662 to the patient's limb.

In contrast to the mechanism discussed above in relation to FIG. 5 for adjusting the height of the fixture, the fixture 600 or front section is allowed to slide up and down within a Delron rack as generally shown in FIG. 6D to form a larger patient support apparatus. As is discussed in greater detail below, the fixture 600 (with a male member) is assembled by sliding it into a back section 690 (female track, left and right), at which time, the opening to the track is capped. This allows the fixture or front section 600 to slide up and down on the back section or plate 690, as is discussed in greater detail below. In order to create steps in this up/down travel, as well as hold it at each step, the front section may be fitted with a pivot arm, with a flat on its underside, and the back plate may be fitted with a series of flat steps (ledges) so that the flat of the pivot arm rests on the flat steps (ledges) of the back plate. This allows for incremental stepping of the front plate. To disengage the pivot arm, handles are provided on both the left and right sides of the fixture bed. These handles pivot the arm back away from the back plate, and disengage the pivot arm from the plate. The means for adjusting the height of the fixture are discussed in detail below with respect to FIGS. 6 and 7.

In assembling the front section 600 to the back section 690, a screw 692 is removed from each side of the rear bottom gusset 640 (see FIG. 6A). This allows the gusset 640 to pivot on the remaining screws. End caps 694 are removed and the front section hooked into guide rails 696 and slidably mounted to the back section 690 to form the patient receiving apparatus. Strips of Velcro 698 may be applied to base plate 602 and mated to foam or other cushiony material that is applied to the surface of base plate 602.

Figure 7A:
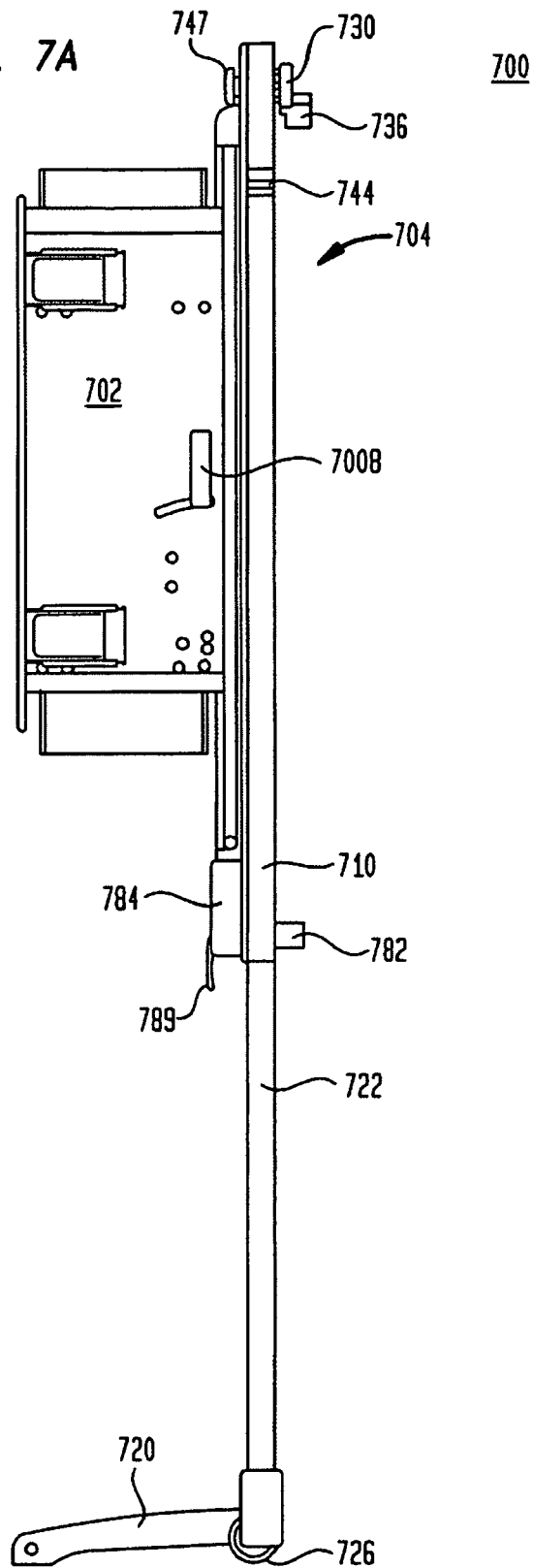
FIG. 7A illustratively depicts a side view of an apparatus in accordance with an aspect of the present invention.
Figure 7F:
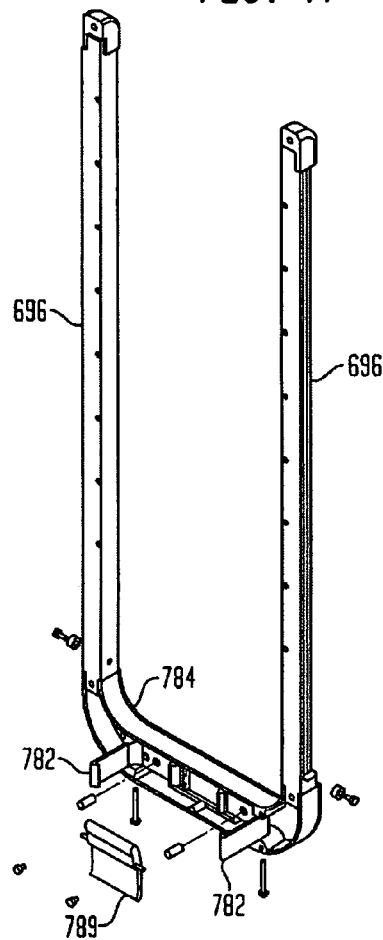
FIGS. 7B through 7G illustratively depicts exploded views of different portions of the apparatus of FIG. 7A in accordance with an aspect of the present invention.
Figure 7B:
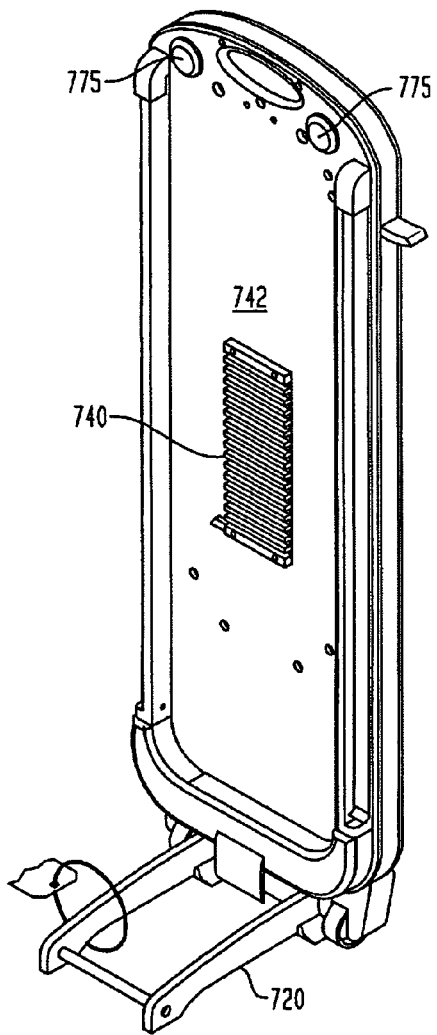

FIG. 7A illustratively depicts a patient receiving apparatus 700 in accordance with a further aspect of the present invention. In particular, FIG. 7A illustratively depicts a side view of a fixture 702 and a docking station or cart 704. The docking station 704 includes a slab 710 (or back section) and a support stand 720. The fixture 702 is mounted to the slab 710. In the position shown in FIG. 7A, the slab 710 and fixture 702 are raised to expose the legs 722 of the docking station 704. For clarity, the legs 722 are also shown in FIG. 6D. As best seen in FIG. 7B, the slab 710 may be lowered so that the legs 722 are fully housed inside the slab 710.

The stand 720 may further include a pair of wheels or casters 726. The docking station 704 conveniently allows the fixture 702 to be mounted to a patient support device, such as device 230, using hooks 730 (one shown). The patient support device conveniently provides a number of docketing ports for the hooks 730. In addition, the patient support device also allows a jumper block 736 that is fitted with connectors that when connected to the patient support provides an indication that the apparatus 700 is mounted. The docking station 704 also allows the fixture 702 to be positioned within the patient receiving space of a magnet resonance imaging magnet without being mounted to a bed.

FIG. 7B also shows a plurality of steps 740 that are formed on an inner side wall 742 of the slab 710. As is explained in greater detail below, the steps 740 provide a means for adjusting the height of the fixture 702. The slab 710 also includes a tab 744 that forms part of a mechanism that raises and lowers the slab 710 (and the fixture 702) between the positions shown in FIGS. 6D and 7B.

Figure 7C:
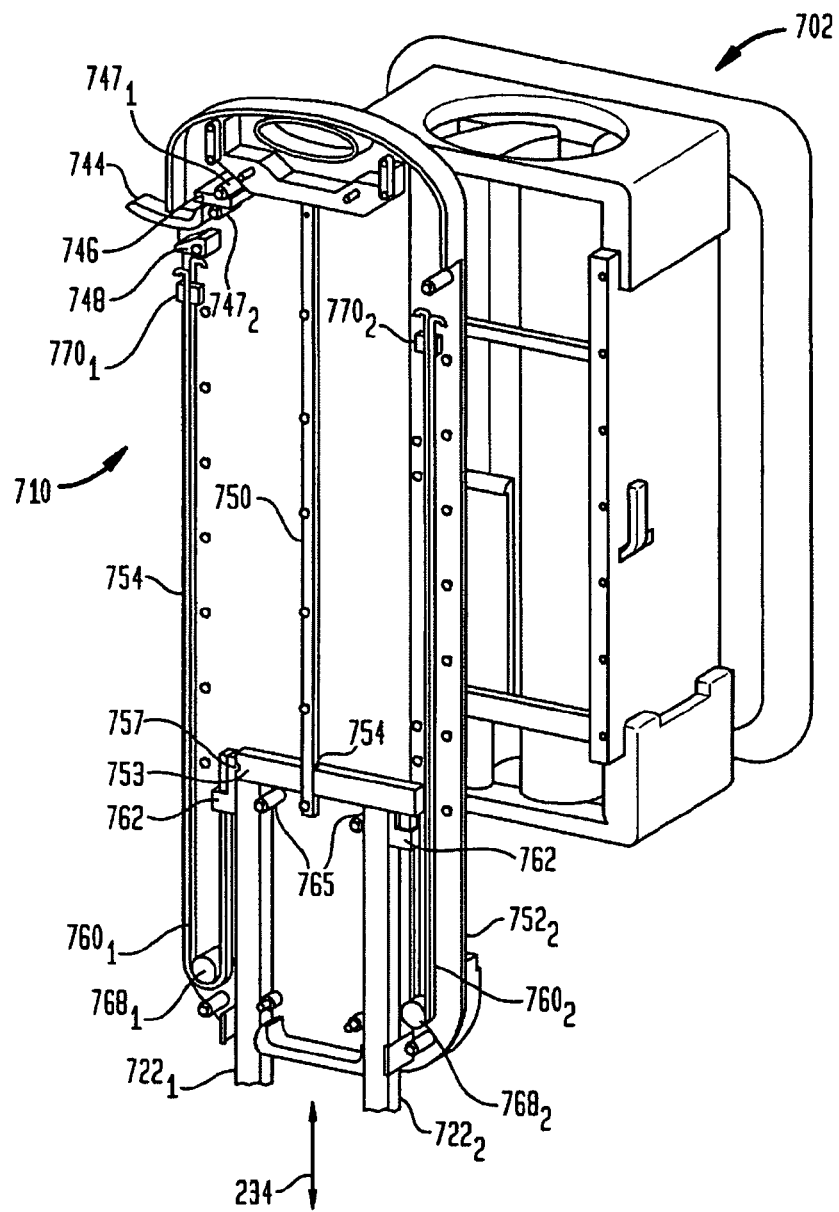
Figure 7D:
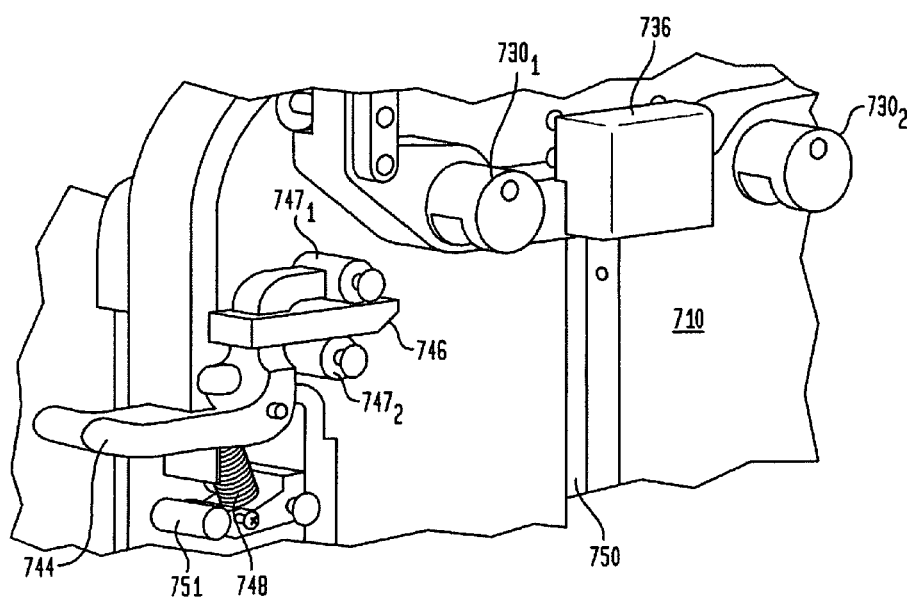

In particular, and as best seen in FIGS. 7C and 7D, the tab 744 is mounted through an arm 746 that extends towards the center of the slab 710. The arm 746 is mounted to translate between a pair of guide rollers $747_1$ and $747_2$. As shown, the tab 744 is mounted using a biasing element 748, which urges the tab upward against the opening 751. When the tab is pressed, it pivots about the biasing element causing arm 746 to retract away from the center of the slab.

As also seen in FIG. 7C, the slab 710 also includes a post 750 mounted at the midpoint between the longitudinal edges $752_1$, $752_2$. A crossbar 753 includes a groove 754 that is formed to mate with the post 750. The groove 754 allows the crossbar 753 to translate along the longitudinal direction 234 with the post 750 functioning as a guide-rail. When the crossbar 753 is positioned proximate the upper end 755 of the slab 710, the arm 746 can engage a notch 757 at the end of the cross-bar 753 and hold the cross-bar 753 in place. When the crossbar 753 is held in place by the arm 746, the legs of the docking station 704 are housed inside the slab as shown in FIG. 7B. On the other hand, when the tab 744 is pressed downward, the arm 746 releases the cross-bar 753, which causes the slab 710 to slide upward over legs 722.

More particularly, the crossbar 753 is connected to the legs 722. The legs 722 are mounted to one end of bungee cords 760 through clamps 762. The side of the legs 722 opposite the clamps 762 is positioned adjacent to rollers 765. The bungee cord 760 is mounted around rollers 768 and secured at its other end to a clamp assembly 770 that is attached to the slab 710. The bungee cords 760 and rollers 768 form a pulley system that reduces the load when the slab 710 and fixture 702 need to be raised to a suitable position. When the notch 757 and arm 746 are engaged the bungee cord is elongated and under maximum tension. When the arm 746 releases the crossbar 753, the bungee cord reverts or contracts thereby pulling the cross bar downward, which causes the slab 710 (and a fixture if connected) to move upward. In operation, the fixture 702 will typically be loaded onto the slab 710 with the legs 722 housed in the slab 710. The fixture 700 may then be rolled to a patient receiving apparatus and mounted thereto.

Figure 7E:
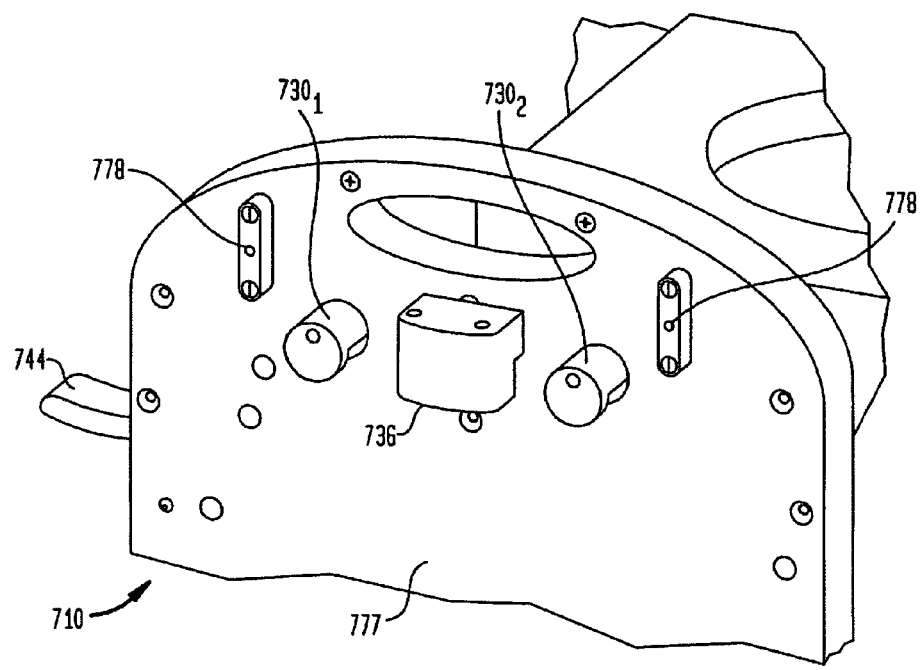

As best seen in FIGS. 7D and 7E, a pair of hooks 730 is mounted to the slab 710. The hooks 730 protrude through the back cover 777 of the slab 710. The hooks 773 are formed and spaced so that they can be mounted into D-slots 260 on the patient receiving apparatus or bed 230 (see FIG. 2). A pair of knobs 775 is mounted through the inner side wall. The knobs 775 are connected to pins 778 as shown in FIG. 7E. The knobs 775 and pin 778 assembly provides an additional mechanism for further securing the fixture 702 and slab 710 to the bed. In particular, once the hooks 773 are aligned with mating slots 260, the knobs 775 and pins 778 are used to prevent the hooks 730 from moving upward by maintaining the pin against the surface 234. In this way, the slab and fixture are further locked in place and prevented from moving upward. FIGS. 7A and 7E also show jumper connector 736, which is used to provide an indication that slab and fixture is locked onto the bed.

In addition, to prevent the docking station 704 from rolling out of the receiving space, a latching mechanism is provided at the lower end of the slab. As seen in FIGS. 6A, 7A and 7F, the latching mechanism comprises a pair of latching tabs 782 that are mounted into the a lower lock housing 784. The housing 784 connects at opposing ends to the front guides 696 for the fixture 702. A handle 789 is mounted through the housing 784 such that when the handle 789 is operated the latching tabs 782 are pushed outward, which unlocks the tabs from slots on the bed 230. When handle 789 is not pressed in toward the slab, the tabs are urged inward and hook onto the bed.

Figure 7G:
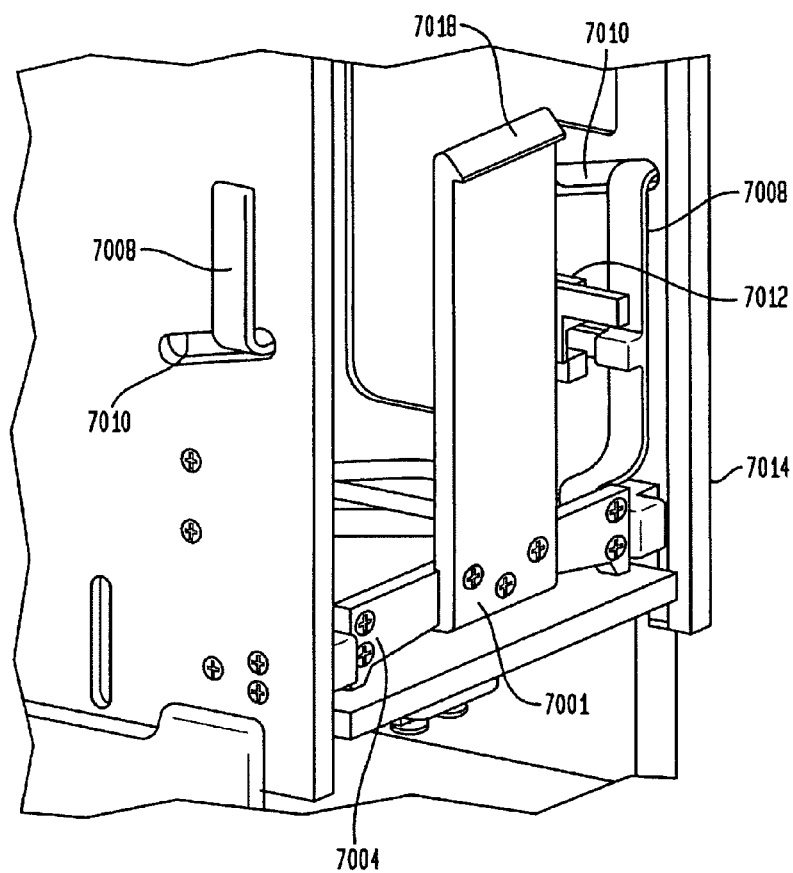

Once the fixture 702 is adjusted to an approximate height to accommodate a patient, the slab is locked into place on the bed. Further adjustments may then be made to the height of the fixture 702 by using a second adjustment mechanism in accordance with an additional aspect of the present invention. In particular, FIG. 7G is an exploded view of the portion of the fixture that is adjacent to the surface 742 in the engaged position. As shown, an arm 7001 is connected to a cross-member 7004, which is pivotally mounted to the sidewalls of the fixture. A pair of handles 7008 protrudes through each sidewall through respective slots 7010. Each handle is further mounted to a sidewall via sub-housing 7012 and spring 7014. Each spring 7014 urges each handle 7008 inward toward the surface 742 in the rest position. The arm 7001 includes a hook 7018 at one end which acts a pawl in each of the steps 740 (see FIG. 7B). In this way, the hook 7018 and steps form a ratchet system that allows the fixture to be adjusted relative to the slab 710.

In particular, when the handle 7008 is pulled away from the slab 710 and bed, the arm pivots away from the steps 740. This allows an operator to adjust the height of the fixture relative to the slab. Once the fixture is appropriately positioned, the handle 7008 may then be released so that the hook 7018 engages one of the steps 740.

Turning now to FIG. 8, where there is shown a stand 800 in accordance with an aspect of the present invention. The stand 700 includes a base portion 804 and a pair of sidewalls 808. The sidewalls 808 project from the base portion 804, as shown. The stand 800 also includes a foldable flap 806. The flap is conveniently located at an end 812 of the stand where support legs 820 are located. The stand 800 forms a part of a docking station as is discussed above.

Additional assembly details of the stand 800 are shown in FIG. 9.

Turning now to FIG. 10, there is shown a support member 1000 that may be used in conjunction with the fixtures discussed above. As indicated by FIGS. 1 and 2 and discussed above, during imaging the patient P will typically stand sideways in the patient receiving space of the magnet. In addition, the patient support device may be rotated so that the patient goes from a standing upright position to a recumbent position. As discussed above, in the recumbent position, the patient's feet and head will need to be supported in order to avoid patient discomfort and movement. The support member 1000 provides support for the head of a patient using the immobilization fixtures discussed above, e.g., fixtures 100, 400, 600 or 702.

Figure 11:
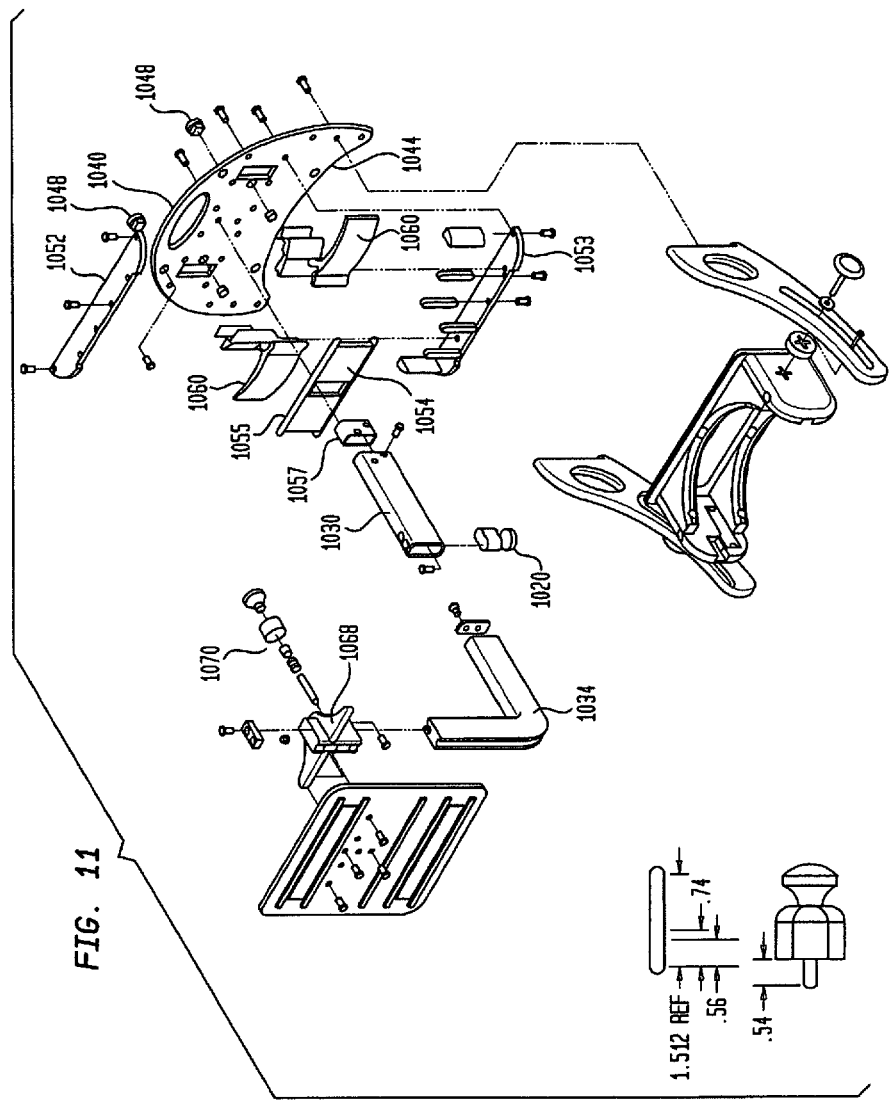
FIG. 11 illustratively depicts an exploded assembly view of the apparatus of FIG. 10 in accordance with an aspect of the present invention.

The head fixture or support member 1000 includes a base 1002, a pair of sidewall members 1006, a support cross-section 1010 and a headrest 1014. The headrest 1014 is connected to the base plate 1002 via an adjustable arm 1018. As best seen in FIG. 11, the arm includes a sleeve 1030 and an L-shaped arm 1034. The L-shaped arm 1034 mounts into the sleeve 1032 and is attached to the headrest 1014. The adjustable arm 1018 includes a locking knob 1020 for locking the headrest 1014 in place. The headrest 1014 is substantially rectangular in shape and preferably includes a pair of Velcro strips 1016 for attaching cushioning (not shown). The cross-section support member 1010 is mounted between the sidewalls 1006 via slots 1022 to allow for adjustment toward and away from the base plate 1002. The support cross-section 1010 is gusseted to accommodate a shoulder of a patient.

Turning now to FIG. 11, there is shown a diagram illustrating the assembly of the support member 1000. As shown, the base 1002 comprises a planar base plate 1040 that includes a circular outer edge 1042 that terminates at a diametric cross section 1044 that includes an arcuate run. The base plate includes a number of screw holes that are used to attach knobs 1048 and compartment 1050. The knobs 1048 are used to attach the support member 1000 to patient support device or bed, e.g., beds 104 or 203.

The compartment 1050 includes top, bottom and front walls 1052; 1053, and 1054. The front wall is attached to the top and bottom walls using fasteners that are mounted through the top and bottom walls and secured in screw holes located along the top and bottom edges of the front wall. The top and bottom walls 1052, 1053 are screwed to the base plate through the appropriate screw holes as shown. The front wall 1054 includes an opening 1055 for receiving the sleeve 1030 of the adjustable arm 1018. The sleeve 1030 is inserted through the opening 1055 onto a mounting stud 1057 and fastened to the mounting stud 1057. The stud 1057 is fastened to the base plate 1040.

The L-shaped arm 1034 is fastened to the headrest 1014 using mounting head 1068. The mounting head 1068 is preferably mounted to the L-shaped arm 1034 using a locking mechanism 1070 as shown. The side walls 1006 are preferably mounted to the support cross-section 1010 using a locking mechanism as shown and previously discussed.

As shown in FIGS. 6 and 7 and discussed above, each of the fixtures, e.g., fixtures 600 and 700, desirably include a bungee mechanism. Where a fixture includes the adjustment features discussed above and strengthening materials that allow the bed or patient support to be rated for 500 lbs., the fixture typically exceeds a weight of 30 lbs. It may be difficult in some circumstance to expect a user to lift a 30+ lb. fixture to dock it on the system bed. As discussed above in relation to FIGS. 6 and 7, a solution to address this concern is to design a secondary body that the main bed section moves up and down in reference to. The fixture may be connected to the secondary body with elastic (bungee) cord, and the cord would be under a set tension, the front section is forced upward by the bungee tension, assisting the user in raising the fixture to the appropriate slab or bed port. As shown, the secondary body preferably has wheels, and allows the fixture to be rolled into place. This alleviates any lifting of the fixture bed. The bungee cord must be magnetically translucent and cannot produce a signal or field that would affect acquiring images. In addition, the cord must have the elasticity, memory set, and durability needed for supporting 30+ lbs of weight.

Figure 13:
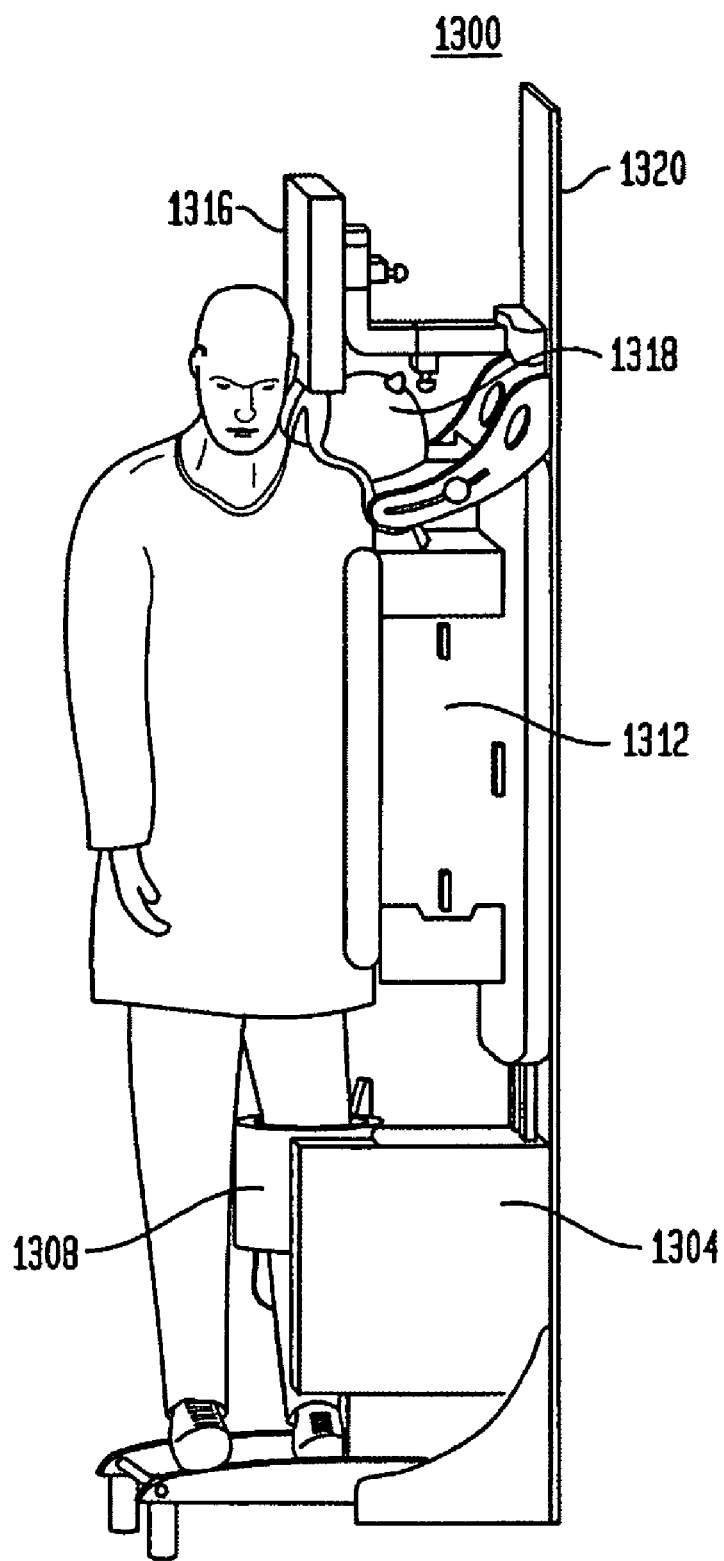
FIG. 13 illustratively depicts a system in accordance with an aspect of the present invention.

Turning now to FIG. 12, there is shown the details of the steps that can be used to assemble a system as discussed above. FIG. 13 shows a partial perspective view of a patient being imaged in a fully assembled system 1300. As shown, the system includes leg support pads 1304. In the embodiment shown, the pads 1304 are gusseted to receive knee coil 1308. The patient is shown standing with an arm inserted in a fixture 1312. In addition, the patient's head is resting against second support fixture 1316. The fixture 1316 may be equipped with a planar RF coil or with a pad that provides a resting surface for the patient's head. A shoulder coil assembly 1318 is attached to the fixture adjacent the patient's shoulder. With the patient supported in this way, the bed 1320 may be rotated about polar axis 228 (see FIG. 2). This rotation allows the patient to be oriented in a variety of imaging positions. For example, the patient may be imaged at 45 degree angle or 60 degree angle of vertical. In addition, by rotating the patient, the patient need not stand during the entire scanning procedure. This may prove particularly advantageous in reducing motion artifacts where the patient's joints are being imaged.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for performing magnetic resonance imaging, comprising:
    attaching a fixture with opposite first and second sides to an elongated patient support apparatus such that the second side is mounted to the elongated patient support apparatus, the elongated patient support apparatus being associated with a magnetic resonance imaging magnet, the magnet defining a static magnetic field direction,;
    positioning a patient adjacent to a cushioned patient support panel of the first side of the fixture such that the patient's anterior to posterior axis is parallel to the static field direction;
    positioning an arm of the patient within an opening, the opening being between the first and second sides such that a lateral side of the patient's torso contacts and is supported by the cushioned patient support panel; and
    scanning a portion of the patient's anatomy.

2. The method of claim 1, further comprising supporting the patient's head and feet against the patient support apparatus and rotating the patient to a recumbent position.

3. The method of claim 2, wherein supporting the patient's head comprises inserting a second fixture to the patient support adjacent the patient's head.

4. The method of claim 1, wherein scanning comprises scanning a patient's shoulder.

5. The method of claim 1, further comprising attaching a second fixture to the patient support apparatus, wherein the second fixture includes a coil.

6. The method of claim 5, further comprising positioning the patient such that the second fixture is adjacent to a shoulder of the patient.

7. The method of claim 5, further comprising positioning the patient such that the patient's head is supported by the second fixture.

8. The method of claim 1, further comprising rotating the elongated patient support to a non-upright position.

9. A device for magnetic resonance imaging, comprising:
    a back plate with a mounting element;
    a front plate, a pair of sidewalls, a top member and a bottom member assembled to form a front section of a substantially rectangular shaped enclosure having at least one opening adapted to receive an arm of a patient, said front section slidably mounted to said back plate to form said enclosure;
    a cylindrical sleeve positioned within the substantially rectangular shaped enclosure such that the cylindrical sleeve is positioned between the back plate and the front plate, wherein one end of the cylindrical sleeve terminates in the at least one opening;
    an arm independently movable from said enclosure, said arm engaging at least one of a series of steps located substantially at the center of said back plate; and
    an elongated patient support of a magnetic resonance scanner with an opening for receiving the mounting element.

10. The device of claim 9, wherein the front section of said enclosure is movable relative to the back plate in a direction substantially parallel to a lengthwise direction defined by the elongated patient support.

11. The device of claim 9, further comprising a handle mounted to the outside of said front section and connected to said independently movable arm.

12. The device of claim 9, wherein the device further comprises a cushioned patient support panel attached to an exterior surface of the front plate.

13. The device of claim 9, further comprising a handle mounted to one sidewall of the pair of sidewalls and connected to said independently movable arm.

14. The device of claim 9, wherein the back plate includes a pulley assembly that moves the enclosure relative to the elongated patient support in a direction substantially parallel to a lengthwise direction defined by the elongated patient support.

15. A device for magnetic resonance imaging, comprising:
    a base plate, a top planar member, a bottom planar member, and a pair of sidewalls assembled so as to form an enclosure, said top planar member having a surface including at least one opening adapted to receive an arm of a patient;
    a mounting rack, said sidewalls mounted to said base plate via said mounting rack, said mounting rack including a front rack, a back rack, a bracket, and a locking mechanism, said bracket fixedly mounted to said front rack, and said back rack fixedly mounted to said base plate, said locking mechanism connected to said mounting rack and disengagably mounted on said back rack, and said front and back rack each include a side adapted to detachably interlock said front and back rack to each other;

a spring mechanism mounted to said base plate through said bracket, said spring mechanism urging said mounting rack against said base plate; and an elongated patient support of a magnetic resonance scanner connected to the back rack of the mounting rack with a locking element such that during magnetic resonance imaging the device reduces movement of the patient's anatomy.

16. The device of claim 15, wherein the device is mounted to the elongated patient support within a Delron rack.

17. The device of claim 16, wherein the elongated patient support is movable into and out of a patient receiving, space of the magnetic resonance imaging scanner.

18. The device of claim 15 wherein said top member, bottom member, pair of sidewalls, bracket and front rack are movable with respect to said base plate and said back rack upon disengaging said locking mechanism from said back rack.

19. The device of claim 15, wherein said enclosure further includes a front section, and wherein a portion of said front section includes a cushioning material.

20. The device of claim 19, wherein said cushioning material is foam.

21. The device of claim 15, further comprising a pair of semi-circular cylindrical members disposed within the enclosure through the at least one opening so as to operate as a sleeve for receiving a patient's arm.

* * * * *